(12) United States Patent
Teboul

(10) Patent No.: US 10,532,021 B2
(45) Date of Patent: Jan. 14, 2020

(54) COMPOSITION COMPRISING A SPECIFIC ACRYLIC POLYMER AND A SILICONE COPOLYMER, AND METHOD FOR TREATING KERATIN FIBRES USING SAME

(71) Applicant: L'OREAL, Paris (FR)

(72) Inventor: Karen Teboul, St Mande (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/367,388

(22) PCT Filed: Dec. 13, 2012

(86) PCT No.: PCT/EP2012/075423
§ 371 (c)(1),
(2) Date: Jun. 20, 2014

(87) PCT Pub. No.: WO2013/092382
PCT Pub. Date: Jun. 27, 2013

(65) Prior Publication Data
US 2015/0125413 A1 May 7, 2015

Related U.S. Application Data

(60) Provisional application No. 61/593,465, filed on Feb. 1, 2012.

(30) Foreign Application Priority Data

Dec. 20, 2011 (FR) ..................................... 11 61996

(51) Int. Cl.
| | | |
|---|---|---|
| A61K 8/895 | (2006.01) | |
| A61Q 5/00 | (2006.01) | |
| A61Q 13/00 | (2006.01) | |
| A61K 8/81 | (2006.01) | |

(52) U.S. Cl.
CPC ............ *A61K 8/895* (2013.01); *A61K 8/8147* (2013.01); *A61Q 5/00* (2013.01); *A61Q 13/00* (2013.01); *A61K 2800/594* (2013.01)

(58) Field of Classification Search
CPC .... A61Q 5/00; A61Q 13/00; A61K 2800/594; A61K 8/895; A61K 8/8147
See application file for complete search history.

(56) References Cited

U.S. PATENT DOCUMENTS

| | | |
|---|---|---|
| 2,463,611 A | 3/1949 | Green et al. |
| 3,175,993 A | 3/1965 | Weyenberg |
| 3,433,232 A | 3/1969 | Garrett |
| 3,599,647 A | 8/1971 | Fabbri |
| 4,578,266 A | 3/1986 | Tietjen et al. |
| 4,693,935 A | 9/1987 | Mazurek |
| 4,728,571 A | 3/1988 | Clemens et al. |
| 4,772,675 A | 9/1988 | Klosowski et al. |
| 4,871,827 A | 10/1989 | Klosowski et al. |
| 4,888,380 A | 12/1989 | Kamis et al. |
| 4,898,910 A | 2/1990 | Kamis et al. |
| 4,906,719 A | 3/1990 | Chu et al. |
| 4,962,174 A | 10/1990 | Bilgrien et al. |
| 4,972,037 A | 11/1990 | Garbe et al. |
| 5,059,414 A | 10/1991 | Dallal et al. |
| 5,162,410 A | 11/1992 | Sweet |
| 5,246,694 A | 9/1993 | Birthwistle |
| 5,645,609 A | 7/1997 | Andrean et al. |
| 5,799,669 A | 9/1998 | Briggs |
| 5,849,318 A | 12/1998 | Imai et al. |
| 5,874,069 A | 2/1999 | Mendolia et al. |
| 5,919,441 A | 7/1999 | Mendolia et al. |
| 5,948,393 A | 9/1999 | Tomomasa et al. |
| 5,961,665 A | 10/1999 | Fishman |
| 5,981,680 A | 11/1999 | Petroff et al. |
| 5,990,479 A | 11/1999 | Weiss et al. |
| 6,013,682 A | 1/2000 | Dalle et al. |
| 6,024,946 A | 2/2000 | Dubief et al. |
| 6,051,216 A | 4/2000 | Barr et al. |
| 6,106,577 A | 8/2000 | Audousset et al. |
| 6,225,198 B1 | 5/2001 | Alivisatos et al. |
| 6,606,943 B2 | 8/2003 | De Laforcade |
| 6,609,457 B1 | 8/2003 | De Laforcade |
| 7,026,424 B2 | 4/2006 | Schafer et al. |
| 7,351,405 B2 | 4/2008 | De La Poterie |
| 7,357,921 B2 | 4/2008 | Giroud |
| 7,537,120 B1 | 5/2009 | Cardenas |
| 7,875,265 B2 | 1/2011 | Blin et al. |
| 7,942,937 B2 | 5/2011 | Brun |
| 8,337,822 B2 | 12/2012 | Brun |
| 2002/0023555 A1 | 2/2002 | Laforcade |
| 2003/0175229 A1 | 9/2003 | Giroud |
| 2004/0120906 A1 | 6/2004 | Toumi et al. |
| 2004/0142831 A1 | 7/2004 | Jager Lezer |
| 2004/0180021 A1 | 9/2004 | De La Poterie |
| 2004/0210024 A1 | 10/2004 | Schafer et al. |
| 2004/0254325 A1 | 12/2004 | Kuepfer et al. |
| 2006/0085924 A1 | 4/2006 | Brun |
| 2006/0093568 A1 | 5/2006 | Blin et al. |
| 2006/0099164 A1 | 5/2006 | De La Poterie et al. |
| 2006/0115444 A1 | 6/2006 | Blin et al. |
| 2006/0116489 A1 | 6/2006 | Lennon |
| 2006/0127334 A1 | 6/2006 | Ferrari et al. |
| 2006/0134032 A1 | 6/2006 | Ilekti et al. |
| 2006/0134044 A1 | 6/2006 | Blin et al. |

(Continued)

FOREIGN PATENT DOCUMENTS

| | | |
|---|---|---|
| CA | 711756 A | 6/1965 |
| EP | 0412704 A2 | 2/1991 |

(Continued)

OTHER PUBLICATIONS

International Search Report for PCT/EP2012/075421, (published as WO 2013/092381), dated Feb. 26, 2013.

(Continued)

*Primary Examiner* — Robert S Cabral
(74) *Attorney, Agent, or Firm* — The Marbury Law Group, PLLC

(57) ABSTRACT

The present invention relates to a non-colouring composition for treating keratin fibres comprising an aqueous dispersion of particles of hybrid hydrophobic acrylic film-forming polymer and a linear block silicone copolymer, and also to a method for treating keratin fibres using such a composition. The composition makes it possible to obtain a coating which is persistent towards shampooing operations, which leaves the treated fibres individualized, with an improved cosmetic feel and a provision of mass and volume.

15 Claims, No Drawings

(56) References Cited

U.S. PATENT DOCUMENTS

| | | |
|---|---|---|
| 2006/0134051 A1 | 6/2006 | Blin et al. |
| 2006/0147402 A1 | 7/2006 | Blin et al. |
| 2006/0147403 A1 | 7/2006 | Ferrari et al. |
| 2006/0216257 A1 | 9/2006 | Pays et al. |
| 2007/0044249 A1 | 3/2007 | Lisowski et al. |
| 2007/0224140 A1 | 9/2007 | Quadir et al. |
| 2008/0171010 A1 | 7/2008 | Brun |
| 2009/0151086 A1 | 6/2009 | Brun |
| 2009/0193595 A1 | 8/2009 | Brun et al. |
| 2009/0214458 A1 | 8/2009 | Brun et al. |
| 2011/0005546 A1 | 1/2011 | Muller-Grunow et al. |
| 2011/0028571 A1 | 2/2011 | Hayakawa |
| 2011/0097289 A1 | 4/2011 | Viala et al. |
| 2011/0165104 A1* | 7/2011 | Molenda ................. A61K 8/44 424/70.9 |
| 2011/0300092 A1 | 12/2011 | Kambach et al. |
| 2013/0074864 A1 | 3/2013 | Nuzzo et al. |
| 2015/0007845 A1 | 1/2015 | Teboul |
| 2015/0132243 A1 | 5/2015 | Teboul |
| 2015/0164196 A1 | 6/2015 | Teboul et al. |
| 2015/0174041 A1 | 6/2015 | Teboul |
| 2015/0174051 A1 | 6/2015 | Teboul |

FOREIGN PATENT DOCUMENTS

| | | |
|---|---|---|
| EP | 0412707 A1 | 2/1991 |
| EP | 0640105 A1 | 3/1995 |
| EP | 0815836 A2 | 1/1998 |
| EP | 0874017 A2 | 10/1998 |
| EP | 1040873 A1 | 10/2000 |
| EP | 1184426 A2 | 3/2002 |
| EP | 1400234 A1 | 3/2004 |
| EP | 1649898 A2 | 4/2006 |
| EP | 2070516 A1 | 6/2009 |
| EP | 2095810 A1 | 9/2009 |
| FR | 2480096 A1 | 10/1981 |
| FR | 2679771 A1 | 2/1993 |
| FR | 2741530 A1 | 5/1997 |
| FR | 2831430 A1 | 5/2003 |
| FR | 2833489 A1 | 6/2003 |
| FR | 2958189 A1 | 10/2011 |
| GB | 2073672 A | 10/1981 |
| JP | 5017710 A | 1/1993 |
| JP | 7258460 A | 10/1995 |
| JP | 9188830 A | 7/1997 |
| JP | 10-158451 A | 6/1998 |
| JP | 10158450 A | 6/1998 |
| JP | 10158541 A | 6/1998 |
| JP | 2004-202251 A | 7/2004 |
| JP | 2008-106067 A | 5/2008 |
| JP | 2008-247761 A | 10/2008 |
| JP | 2008-247879 A | 10/2008 |
| JP | 2010-524917 A | 7/2010 |
| JP | M10-524917 A | 7/2010 |
| WO | 9221316 A1 | 12/1992 |
| WO | 93/23446 A2 | 11/1993 |
| WO | 9500578 A1 | 1/1995 |
| WO | 0196450 A2 | 12/2001 |
| WO | 03014194 A1 | 2/2003 |
| WO | 2004028487 A2 | 4/2004 |
| WO | 2008/142658 A2 | 11/2008 |
| WO | 2010071777 A1 | 6/2010 |
| WO | 2013092380 A1 | 6/2013 |
| WO | 2013092381 A1 | 6/2013 |
| WO | 2013092788 A1 | 6/2013 |
| WO | 2014/001390 A1 | 1/2014 |
| WO | 2014/001391 A1 | 1/2014 |

OTHER PUBLICATIONS

International Search Report for PCT/EP2012/076269, (published as WO 2013/092788), dated Feb. 25, 2013.
International Search Report for PCT/EP2012/075419, (published as WO 2013/092380), dated May 8, 2013.
International Search Report for PCT/EP2012/075423, (published as WO 2013/092382), dated Feb. 28, 2013.
English language abstract for JP 5017710.
English language abstract for JP 7258460.
English language abstract for JP 9188830.
English language abstract for JP 10158541.
English language abstract for JP 10158450.
"Perfumes," Kirk-Othmer Encyclopedia of Chemical Technology, Fourth Edition, vol. 18, 1996, pp. 171-200.
Todd, Charles et al., "Volatile silicone fluids for cosmetic formulations," Cosmetics and Toiletries, Feb. 1990, vol. 105, pp. 53-64.
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
Peng, Xiaogang et al., "Epitaxial Growth of Highly Luminescent CdSE/CdS Core/Shell Nanocrystals with Photostability and Electronic Accessibility," Journal of the American Chemical Society, vol. 119, No. 30, pp. 7019-7029.
Find Office Action for co-pending U.S. Appl. No. 14/367,382 (dated Nov. 25, 2016).
Final Office Action for copending U.S. Appl. No. 14/367,376, dated Dec. 21, 2018.
Moss et al., Silicones as a Color-Lock Aid in Rinse-Off Hair Care Products, obtained online at: https//pdfs.semanticscholar.org/e78b/faa5983618b3b3896ad83c50e16167513de.pdf (Year 2004).
Final Office Action for co-pending U.S. Appl. No. 14/411,671, dated Apr. 19, 2019.
Final Office Action for copending U.S. Appl. No. 14/411,679, dated Oct. 2, 2018.
Non-Final Office Action for copending U.S. Appl. No. 14/411,671, dated Oct. 3, 2018k.
Final Office Action for copending U.S. Appl. No. 14/367,370, dated Nov. 19, 2018.
Fang, K. et al., "New high molecular weight silicone polyether emulsions for use in personal care applications," IPCOM000200095D, Sep. 27, 2010.
Final Office Action for copending U.S. Appl. No. 14/367,382, dated Aug. 6, 2018.
Non-Final Office Action for co-pending U.S. Appl. No. 14/411,679, dated Apr. 5, 2019.
Non-Final Office Action for copending Application No. 14/411,679, mailed Oct. 12, 2016.
Non-Final Office Action for co-pending U.S. Appl. No. 14/367,376, dated Aug. 15, 2019.
Final Office Action for co-pending U.S. Appl. No. 14/367,370, dated Jul. 11, 2019.
Final Office Action for copending U.S. Appl. No. 14/367,370, dated Nov. 3, 2016.
Machine Translation of Notification of Reasons for Refusal for counterpart Japanese Application No. 2014-547862, dated Nov. 10, 2016.
Machine Translation of Notification of Reasons for Refusal for counterpart Japanese Application No. 2014-547861, dated Nov. 21, 2016.
Machine Translation of Notification of Reasons for Refusal for counterpart Japanese Application No. 2014-547863, dated Nov. 14, 2016.
Machine Translation of Chinese First Office Action for counterpart Chinese Application No. 201380034562.1, dated Jan. 12, 2016.
Machine Translation of Chinese Second Office Action for counterpart Chinese Application No. 201380034562.1, dated Nov. 30, 2016.
Machine Translation of Chinese First Office Action for counterpart Chinese Application No. 201380034576.3, dated Dec. 31, 2015.
Machine Translation of Chinese Second Office Action for counterpart Chinese Application No. 201300345676.3, dated Nov. 17, 2016.
Machine Translation of Chinese Third Office Action for counterpart Chinese Application No. 201280062545, dated Apr. 10, 2017.
Final Office Action for copending U.S. Appl. No. 14/367,370, dated Jun. 16, 2017.

(56) References Cited

OTHER PUBLICATIONS

Final Office Action for copending U.S. Appl. No. 14/367,370, dated Jan. 12, 2018.
Final Office Action for copending U.S. Appl. No. 14/367,376, dated Jul. 3, 2017.
Non-Final Office Action for copending U.S. Appl. No. 14/367,382, dated Nov. 16, 2017.
Non-Final Office Action for copending U.S. Appl. No. 14/411,679, dated Nov. 30, 2017.
Office Action for counterpart European Application No. 12 799 223.8, dated Jun. 1, 2017.
Non-Final Office Action for copending U.S. Appl. No. 14/411,671, dated Jun. 16, 2017.
Shin-Etsu, "Shin-Etsu Unique Materials," Shin-Etsu, revised Nov. 2010, 20 pages.
Chinese Office Action for counterpart Chinese Application No. 201380034576.3, dated Feb. 5, 2018 (translation unavailable).
Final Office Action for copending U.S. Appl. No. 14/411,671, dated Apr. 6, 2018.
International Search Report and Written Opinion for PCT/EP2013/063387, dated Jan. 8, 2013.
International Search Report and Written Opinion for PCT/EP2013/063388, dated Jan. 8, 2013.
Non-Final Office Action for copending U.S. Appl. No. 14/367,376, dated Sep. 17, 2015.
Final Office Action for copending U.S. Appl. No. 14/367,376, dated May 20, 2016.
Non-Final Office Action for copending U.S. Appl. No. 14/367,382, dated Feb. 24, 2016.
Non-Final Office Action for copending U.S. Appl. No. 14/367,370, dated Feb. 2, 2016.
Final Office Action for co-pending U.S. Appl. No. 14/367,382 (dated Nov. 25, 2016).
Non-Final Office Action for co-pending U.S. Appl. No. 14/367,376 (dated Dec. 1, 2016).

* cited by examiner

COMPOSITION COMPRISING A SPECIFIC ACRYLIC POLYMER AND A SILICONE COPOLYMER, AND METHOD FOR TREATING KERATIN FIBRES USING SAME

This is a national stage application of PCT/EP2012/075423, filed internationally on Dec. 13, 2012, which claims priority to U.S. Provisional Application No. 61/593,465, filed on Feb. 1, 2012, as well as French Application No. 1161996, filed Dec. 20, 2011, all of which are incorporated herein by reference in their entireties.

The present invention relates to a non-colouring composition for treating keratin fibres comprising an aqueous dispersion of particles of a specific acrylic polymer and a linear block silicone copolymer, and also to a method for treating keratin fibres using said composition.

The hair is generally damaged and embrittled by the action of external atmospheric agents such as light and inclement weather, and by mechanical or chemical treatments, such as brushing, combing, bleaching, permanent-waving and/or dyeing. The result of this is that the hair is often difficult to manage and in particular is difficult to disentangle or to style, and a head of hair, even a thick head of hair, struggles to maintain an attractive style due to the fact that the hair lacks vigour, volume and liveliness.

This deterioration in the hair is furthermore increased by the repetition of permanent hair colouring treatments, which consists in applying, to the hair, one or more dye precursors and an oxidizing agent.

Thus, in order to overcome this, it is now normal to use styling products which make it possible to condition the hair by giving it in particular body, mass or volume.

These styling products are generally cosmetic hair compositions comprising one or more polymers which have a strong affinity for the hair and which usually have the function of forming a film on the surface of the hair for the purpose of modifying its surface properties, in particular in order to condition it or in order to impart specific optical properties thereto.

One disadvantage related to the use of these hair compositions lies in the fact that the cosmetic effects conferred by such compositions have a tendency to disappear, in particular starting from the first shampooing operation.

In order to overcome this disadvantage, it is possible to envisage increasing the persistence of the deposited layer of polymers by directly carrying out a radical polymerization of certain monomers on the hair. However, the treatments thus obtained result in a deterioration in the fibre and the hair thus treated is generally difficult to disentangle.

Furthermore, it is known to coat the hair using a composition comprising an electrophilic monomer of cyanoacrylate type, in particular in Patent Application FR 2 833 489. Such a composition makes it possible to obtain completely coated and non-greasy hair. However, the coating obtained requires specific operating conditions, due to the reactivity of the electrophilic monomer. Furthermore, the coating obtained with these electrophilic monomers becomes tacky with fatty substances, such as sebum.

It is also known, in particular from the document EP 2 095 810, to improve the persistence of the deposited layer on the keratin fibres by application of a composition comprising a pressure-sensitive adhesive silicone copolymer, better known under the name of BioPSA. The feel obtained with these copolymers is generally tacky. The hair treated with this type of composition exhibits a slightly coarse, not completely natural, feel. Furthermore, the application of this type of composition is time-consuming and requires a stage of complete drying at a temperature above ambient temperature, for example with a hair dryer, necessary in order to obtain the persistent coating.

Document WO92/21316 describes compositions based on silicone and latexes. The results obtained from the compositions of this document are not, however, satisfactory in terms of coating effect and persistence of the properties, in particular with regard to shampooing operations.

Moreover, hair treatment products (gels, shampoos, hair care or conditioning products) are generally scented but exhibit a very limited persistence of the fragrance on the head of hair, the fragrance generally fading after a few minutes or, in the best of cases, a few hours.

Thus, the aim of the present invention is to develop a composition for treating keratin fibres, in particular human keratin fibres, such as the hair, which makes it possible to obtain coatings which are persistent towards shampooing operations and towards the various attacks which the hair may be subjected to, in particular blow drying operations and perspiration, while exhibiting better toleration towards fatty substances, such as sebum, and while not developing a tacky nature, this coating furthermore being homogeneous and smooth on the keratin fibres, leaving the latter completely individualized.

This aim is achieved with the present invention, one subject of which is thus a non-colouring treatment composition comprising at least one aqueous dispersion of particles of at least one hybrid hydrophobic film-forming acrylic polymer and at least one linear block silicone copolymer.

Another subject of the invention is a method for treating keratin fibres comprising the application, to the fibre or fibres, of the composition of the invention, the application optionally being followed by a drying of the fibres.

The term "at least one" is understood to mean "one or more".

The term "non-colouring composition" is understood to mean a composition which does not confer, on the keratin fibres, a new colour via one or more colorants. The composition according to the invention thus does not contain such colorants and in particular contains neither pigments nor oxidation dyes and, if it comprises soluble direct dyes, does so at a concentration (generally less than 0.005%) such that the composition is coloured without a colouring effect on the keratin fibres.

The treatment composition of the invention makes it possible to obtain a coating which is persistent towards shampooing operations while preserving the physical qualities of the keratin fibre. Such a coating is in particular resistant to the external attacks which the fibres may be subjected to, such as blow drying and perspiration. It makes it possible in particular to obtain a smooth and homogeneous deposited layer. With the composition and method of the invention, a persistent coating is obtained without it being necessary to dry the hair with a hair dryer. The hair, after application, is left in the open air; after a few seconds, the persistent coating is formed. The hairs are individualized.

The term "individualized fibres" is understood to mean fibres which, after application of the composition and drying, are not stuck together (or are all separated from one another) and thus do not form clumps, the coating being formed around virtually each fibre.

Aqueous Dispersion of Particles of Hybrid Acrylic Hydrophobic Film-Forming Polymer The term "polymer" is understood to mean, within the meaning of the invention, a compound corresponding to the repetition of one or more units (these units resulting from compounds known as monomers). This or these unit(s) is (are) repeated at least twice and preferably at least 3 times.

The term "film-forming polymer" is understood to mean a polymer which is capable of forming, by itself alone or in the presence of an additional film-forming agent, a macroscopically continuous film on a support, in particular on keratin substances, and preferably a cohesive film.

The term "hydrophobic polymer" is understood to mean a polymer having a solubility in water at 25° C. of less than 1% by weight.

The dispersion can be a simple dispersion in the aqueous medium of the composition. Mention may be made, as specific case of dispersions, of latexes.

The term "hybrid acrylic polymer" is understood to mean, within the meaning of the present invention, a polymer synthesized from at least one compound (i) chosen from monomers having at least one (meth)acrylic acid group and/or esters of these acid monomers and/or amides of these acid monomers and from at least one compound (ii) other than the compounds (i), i.e. which does not comprises (meth)acrylic acid group and/or esters of these acid monomers and/or amides of these acid monomers.

The (meth)acrylic acid esters (also known as (meth) acrylates) are advantageously chosen from alkyl (meth) acrylates, in particular $C_1$-$C_{30}$, preferably $C_1$-$C_{20}$ and better still $C_1$-$C_{10}$ alkyl (meth)acrylates, aryl (meth)acrylates, in particular $C_6$-$C_{10}$ aryl (meth)acrylates, or hydroxyalkyl (meth)acrylates, in particular $C_2$-$C_6$ hydroxyalkyl (meth) acrylates.

Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate.

Mention may be made, among aryl (meth)acrylates, of benzyl acrylate and phenyl acrylate.

The (meth)acrylic acid esters which are particularly preferred are the alkyl (meth)acrylates.

According to the present invention, the alkyl group of the esters can be either fluorinated or perfluorinated, that is to say that some or all of the hydrogen atoms of the alkyl group are replaced with fluorine atoms.

Mention may be made, as amides of the acid monomers, for example, of (meth)acrylamides and in particular N-alkyl (meth)acrylamides, especially N—($C_2$-$C_{12}$ alkyl)(meth) acrylamides. Mention may be made, among N-alkyl(meth) acrylamides, of N-ethylacrylamide, N-(t-butyl)acrylamide, N-(t-octyl)acrylamide and N-undecylacrylamide.

Mention will be made, as compounds (ii) other than the compounds (i), for example, of styrene monomers.

In particular, the acrylic polymer can be a styrene/acrylate copolymer and especially a polymer chosen from the copolymers resulting from the polymerization of at least one styrene monomer and at least one $C_1$-$C_{20}$ and preferably $C_1$-$C_{10}$ alkyl acrylate.

Mention may be made, as styrene monomer which can be used in the invention, of styrene or α-methylstyrene and preferably styrene.

The $C_1$-$C_{10}$ alkyl acrylate monomer can be chosen from methyl acrylate, ethyl acrylate, propyl acrylate, butyl acrylate, hexyl acrylate, octyl acrylate or 2-ethylhexyl acrylate.

Mention may be made, as acrylic polymer synthesized with styrene monomers, of the styrene/acrylate(s) copolymers sold under the name Joncryl 77 by BASF, under the name Yodosol GH41F by Akzo Nobel and under the name Syntran 5760 CG by Interpolymer.

Mention may also be made, as compound (ii), of the compounds which interact by a process other than the radical polymerization of unsaturated compounds or the compounds resulting from such a process. Such a process can, for example, be a polycondensation. Mention may be made, as polycondensation, of the formation of polyurethanes, polyesters or polyamides. In addition to the acrylic monomer or monomers, the hybrid hydrophobic film-forming polymer of the invention will then contain the compound resulting from the condensation process or the compounds which interact in the polycondensation process.

Mention may in particular be made, as film-forming hybrid acrylic copolymers of this type, of the product sold under the reference Hybridur 875 Polymer Dispersion by Air Products and Chemicals.

Use may also be made, as hybrid film-forming hydrophobic acrylic copolymer, of the product sold under the reference Primal HG 1000 by Dow.

According to one particular embodiment, the hybrid film-forming acrylic polymer is a copolymer based on at least one styrene monomer and at least one (meth)acrylic acid ester.

The hybrid hydrophobic film-forming acrylic polymer or polymers in aqueous dispersion can be present in a content, as polymer active materials, ranging from 0.1% to 30% by weight, better still from 0.5% to 20% by weight and even better still from 1% to 15% by weight, relative to the total weight of the composition.

Linear Block Silicone Copolymer

The silicone copolymer used in the composition according to the invention is a linear block copolymer, that is to say an uncrosslinked copolymer, obtained by chain extension and not by crosslinking.

The term "block copolymer" (or "sequential copolymer") denotes a polymer comprising at least two distinct blocks (sequences). Each block of the polymer results from one type of monomer or from several types of different monomers. This means that each block can be composed of a homopolymer or of a copolymer, it being possible for this copolymer constituting the block to be in its turn a random or alternating copolymer.

The silicone copolymer used in the composition according to the invention preferably comprises at least two distinct silicone blocks, each block of the polymer resulting from one type of silicone monomer or from several types of different silicone monomers, such as mentioned below.

It should also be noted that the copolymer is "linear"; in other words, the structure of the polymer is neither branched nor star-shaped nor grafted.

The linear block silicone copolymer is advantageously provided in the form of particles in dispersion in an aqueous medium.

The aqueous dispersion of block copolymer particles is a silicone-in-water (Sil/W) emulsion, the oily globules of which are composed of a silicone of high viscosity, so that these globules appear to form "soft particles".

The size of the linear block silicone copolymer particles can vary widely. Preferably, in the present patent application, the linear block silicone copolymer particles generally have a number-average size of less than or equal to 2 microns and preferably of less than or equal to 1 micron.

The aqueous dispersions of linear block silicone copolymer particles used in the composition according to the invention can be chosen in particular from those described in document EP-A-874 017, the teaching of which is incorporated here by reference. According to this document, it is possible in particular to obtain the silicone copolymers constituting these particles by a chain extension reaction in the presence of a catalyst, starting from at least:

(a) one polysiloxane (i) having at least one reactive group and preferably one or two reactive groups per molecule; and (b) one organosilicone compound (ii) which reacts with the polysiloxane (i) by a chain extension reaction.

In particular, the polysiloxane (i) is chosen from the compounds of formula (I):

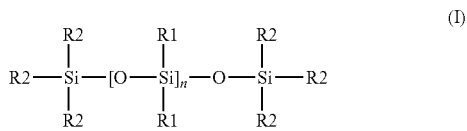

(I)

in which $R_1$ and $R_2$ represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" is understood to mean any group capable of reacting with the organosilicone compound (ii) to form a block copolymer. Mention may be made, as reactive groups, of hydrogen; aliphatically unsaturated groups, in particular vinyl, allyl or hexenyl groups; the hydroxyl group; alkoxy groups, such as methoxy, ethoxy or propoxy groups; alkoxy-alkoxy groups; the acetoxy group; amino groups, and mixtures thereof. Preferably, more than 90% and better still more than 98% of reactive groups are at the chain end, that is to say that the $R_2$ radicals generally constitute more than 90% and even 98% of the reactive groups.

n can in particular be an integer ranging from 5 to 30, preferably from 10 to 30 and better still from 15 to 25.

The polysiloxanes of formula (I) are linear polymers, that is to say comprising few branchings and generally less than 2 mol % of siloxane units. Furthermore, the $R_1$ and $R_2$ groups can optionally be substituted by amino groups, epoxy groups or sulfur-comprising, silicon-comprising or oxygen-comprising groups.

Preferably, at least 80% of the $R_1$ groups are alkyl groups and better still methyl groups.

Preferably, the reactive group $R_2$ at the chain end is an aliphatically unsaturated group and in particular a vinyl group.

Mention may in particular be made, as polysiloxanes (i), of dimethylvinylsiloxy-polydimethylsiloxane, a compound of formula (I) in which the $R_1$ radicals are methyl radicals and the $R_2$ radicals at the chain end are vinyl radicals while the other two $R_2$ radicals are methyl radicals.

The organosilicone compound (ii) can be chosen from polysiloxanes of formula (I) or compounds acting as chain-extending agent. If it is a compound of formula (I), the polysiloxane (i) will comprise a first reactive group and the organosilicone compound (ii) will comprise a second reactive group which will react with the first. If it is a chain-extending agent, it can be a silane, a siloxane (disiloxane or trisiloxane) or a silazane. Preferably, the organosilicone compound (ii) is a liquid organohydropolysiloxane of formula (II):

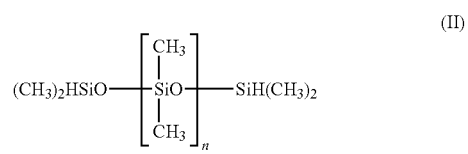

(II)

where n is an integer greater than 1 and preferably greater than 10, for example ranging from 2 to 100, preferably from 10 to 30 and better still from 15 to 25. According to a specific embodiment of the invention, n is equal to 20.

The silicone block copolymers used according to the invention are advantageously devoid of oxyalkylene groups, in particular devoid of oxyethylene and/or oxypropylene groups.

The catalyst of the reaction between the polysiloxane and the organosilicone compound can be chosen from metals and in particular from platinum, rhodium, tin, titanium, copper and lead. It is preferably platinum or rhodium.

The dispersion of silicone copolymer particles used in the composition according to the invention can in particular be obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture, in order for the chain-extending reaction to begin only in the dispersion.

Mention may be made, as emulsifiers capable of being used in the preparation process described above in order to obtain the aqueous dispersion of particles, of non-ionic or ionic (anionic, cationic or amphoteric) emulsifiers. They are preferably non-ionic emulsifiers which can be chosen from polyalkylene glycol ethers of fatty alcohols comprising from 8 to 30 carbon atoms and preferably from 10 to 22 carbon atoms; polyoxyalkylenated and in particular polyoxyethylenated sorbitan alkyl esters, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and mixtures thereof. The amount of emulsifier(s) is generally from 1% to 30% by weight, relative to the total weight of the reaction mixture.

The emulsifier used to obtain the aqueous dispersion of particles is preferably chosen from polyethylene glycol ethers of fatty alcohols and mixtures thereof, and in particular polyethylene glycol ethers of alcohols comprising 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3, $C_{12}$-$C_{13}$ Pareth-23 and mixtures thereof.

According to a specific embodiment of the invention, the dispersion of silicone copolymer particles is obtained from dimethylvinylsiloxy-polydimethylsiloxane (or divinyldimethicone), as compound (i), and from the compound of formula (II) with preferably n=20, as compound (ii), preferably in the presence of a catalyst of platinum type, and the dispersion of particles is preferably obtained in the presence of $C_{12}$-$C_{13}$ Pareth-3 and $C_{12}$-$C_{13}$ Pareth-23, as emulsifiers.

Use may in particular be made, as dispersion of silicone copolymer particles, of the product sold under the name HMW 2220 by Dow Corning (CTFA name: divinyldimethicone/dimethicone copolymer/$C_{12}$-$C_{13}$ Pareth-3/$C_{12}$-$C_{13}$ Pareth-23), which is a 60% aqueous dispersion of divinyldimethicone/dimethicone copolymer comprising $C_{12}$-

$C_{13}$ Pareth-3 and $C_{12}$-$C_{13}$ Pareth-23, said dispersion comprising approximately 60% by weight of copolymer, 2.8% by weight of $C_{12}$-$C_{13}$ Pareth-23, 2% by weight of $C_{12}$-$C_{13}$ Pareth-3 and 0.31% by weight of preservatives, the remainder to 100% being water.

The linear block silicone copolymer or copolymers can be present, for example, in an amount, as polymeric active materials, ranging from 0.1% to 30% by weight, better still from 0.5% to 20% by weight and even better still from 1% to 15% by weight, relative to the total weight of the composition.

According to one embodiment, the hybrid hydrophobic film-forming acrylic polymer or polymers and the linear block silicone copolymer or copolymers are present in a hybrid hydrophobic film-forming acrylic polymer(s) to linear block silicone copolymer(s) weight ratio (as polymer active materials) ranging from 0.2 to 10, better still from 0.5 to 5 and even better still from 1 to 3.

When the hybrid hydrophobic film-forming acrylic polymer has a glass transition temperature which is too high for the desired use, for example a Tg above 40° C., a plasticizer can be combined therewith so as to lower this temperature of the mixture used. The plasticizer can be chosen from the plasticizers normally used in the field of application and in particular from compounds which can be solvents for the polymer.

Preferably, the plasticizer has a molecular weight of less than or equal to 5000 g/mol, preferably of less than or equal to 2000 g/mol, preferably of less than or equal to 1000 g/mol and more preferably of less than or equal to 900 g/mol. The plasticizer advantageously has a molecular weight of greater than or equal to 100 g/mol.

Thus, the composition can additionally comprise at least one plasticizing agent. In particular, mention may be made, alone or as a mixture, of the usual plasticizers, such as:
- glycols and derivatives thereof, such as diethylene glycol ethyl ether, diethylene glycol methyl ether, diethylene glycol butyl ether or diethylene glycol hexyl ether, ethylene glycol ethyl ether, ethylene glycol butyl ether or ethylene glycol hexyl ether;
- polyethylene glycols, polypropylene glycols, polyethylene glycol/polypropylene glycol copolymers and mixtures thereof, in particular polypropylene glycols of high molecular weight, for example having a molecular weight ranging from 500 to 15 000, such as, for example:
- glycol esters;
- propylene glycol derivatives and in particular propylene glycol phenyl ether, propylene glycol diacetate, dipropylene glycol ethyl ether, tripropylene glycol methyl ether, diethylene glycol methyl ether or dipropylene glycol butyl ether. Such compounds are sold by Dow Chemical under the names Dowanol PPH and Dowanol DPnB;
- acid esters, in particular carboxylic acid esters, such as citrates, phthalates, adipates, carbonates, tartrates, phosphates or sebacates;
- esters resulting from the reaction of a monocarboxylic acid of formula $R_{11}COOH$ with a diol of formula $HOR_{12}OH$ with $R_{11}$ and $R_{12}$, which are identical or different, representing a saturated or unsaturated and linear, branched or cyclic hydrocarbon chain preferably comprising from 3 to 15 carbon atoms and optionally comprising one or more heteroatoms, such as N, O or S, in particular the monoester resulting from the reaction of isobutyric acid and octanediol, such as 2,2,4-trimethyl-1,3-pentanediol, such as that sold under the reference Texanol Ester Alcohol by Eastman Chemical;
- oxyethylenated derivatives, such as oxyethylenated oils, in particular vegetable oils, such as castor oil;
- mixtures thereof.

More particularly, the plasticizer can be chosen from esters of at least one carboxylic acid comprising from 1 to 7 carbon atoms and of a polyol comprising at least 4 hydroxyl groups.

The polyol according to the invention can be a cyclized or non-cyclized monosaccharide—polyhydroxyaldehyde (aldose) or polyhydroxyketone (ketose). The polyol is preferably a cyclized monosaccharide in the hemiacetal form.

The polyol can be a mono- or polysaccharide comprising from 1 to 10 monosaccharide units, preferably from 1 to 4 monosaccharide units and more preferably one or two monosaccharide units. The polyol can be chosen from erythritol, xylitol, sorbitol, glucose, sucrose, lactose or maltose.

The polyol according to the invention is preferably a disaccharide. Mention may be made, among disaccharides, of sucrose (also known as α-D-glucopyranosyl-(1-2)-β-D-fructofuranose), lactose (also known as β-D-galactopyranosyl-(1-4)β-D-glucopyranose) and maltose (also known as α-D-glucopyranosyl-(1-4)β-D-glucopyranose), and preferably of sucrose.

The ester according to the invention can be composed of a polyol esterified by at least two different monocarboxylic acids or by at least three different monocarboxylic acids.

The ester according to the invention can be a copolymer of two esters, in particular a copolymer i) of a sucrose substituted by benzoyl groups and ii) of a sucrose substituted by acetyl and/or isobutyryl groups.

The carboxylic acid is preferably a monocarboxylic acid comprising from 1 to 7 carbon atoms and preferably from 1 to 5 carbon atoms, for example chosen from acetic acid, n-propanoic acid, isopropanoic acid, n-butanoic acid, isobutanoic acid, tert-butanoic acid, n-pentanoic acid and benzoic acid.

The ester can be obtained from at least two different monocarboxylic acids. According to one embodiment, the acid is a linear or branched acid which is unsubstituted.

The acid is preferably chosen from acetic acid, isobutyric acid, benzoic acid and mixtures thereof.

According to a preferred embodiment, the ester is sucrose diacetate hexa(2-methylpropanoate), such as that sold under the name Sustane SAIB Food Grade Kosher by Eastman Chemical.

According to another embodiment, the plasticizer can be chosen from esters of an aliphatic or aromatic polycarboxylic acid and of an aliphatic or aromatic alcohol comprising from 1 to 10 carbon atoms.

The aliphatic or aromatic alcohol comprises from 1 to 10 carbon atoms, preferably from 1 to 8 carbon atoms, for example from 1 to 6 carbon atoms. It can be chosen from R1OH alcohols, such that R1 represents methyl, ethyl, propyl, isopropyl, butyl, hexyl, ethylhexyl, decyl, isodecyl, benzyl or benzyl substituted by an alkyl comprising from 1 to 3 carbon atoms, and mixtures thereof.

The aliphatic or aromatic polycarboxylic acid preferably comprises from 3 to 12 carbon atoms, preferably from 3 to 10 carbon atoms, preferably from 3 to 8 carbon atoms, for example 6 or 8 carbon atoms.

The aliphatic or aromatic polycarboxylic acid is advantageously chosen from dicarboxylic acids and tricarboxylic acids.

Mention may be made, among aliphatic dicarboxylic acids, of those of formula HOOC—(CH$_2$)$_n$—COOH, in which n is an integer ranging from 1 to 10, preferably ranging from 2 to 8, for example equal to 2, 4, 6 or 8.

Preference is given to dicarboxylic acids chosen from succinic acid, adipic acid and sebacic acid.

Mention may be made, among aromatic dicarboxylic acids, of phthalic acid.

Mention may be made, among tricarboxylic acids, of triacids which correspond to the formula:

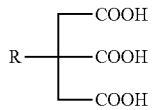

in which R represents an —H, —OH or —OCOR' group in which R' represents an alkyl group having from 1 to 6 carbon atoms. Preferably, R represents an —OCOCH$_3$ group.

The tricarboxylic acid is chosen in particular from acetylcitric acid, butyroylcitric acid or citric acid.

Use may be made, among tricarboxylic acid esters, of esters derived from citric acid (or citrates), such as tributyl acetylcitrate, triethyl acetylcitrate, triethylhexyl acetylcitrate, trihexyl acetylcitrate, trihexyl butyroylcitrate, triisodecyl citrate, triisopropyl citrate, tributyl citrate and tri(2-ethylhexyl) citrate. Mention may be made, as commercial references for plasticizers mentioned above, of the Citroflex range sold by Vertellus, with in particular Citroflex A4 and Citroflex C2.

Mention may be made, among adipic acid esters, of dibutyl adipate and di(2-ethylhexyl) adipate.

Mention may be made, among sebacic acid esters, of dibutyl sebacate, di(2-ethylhexyl) sebacate, diethyl sebacate and diisopropyl sebacate.

Mention may be made, among succinic acid esters, of di(2-ethylhexyl) succinate and diethyl succinate.

Mention may be made, among phthalic acid esters, of benzyl butyl phthalate, dibutyl phthalate, diethylhexyl phthalate, diethyl phthalate and dimethyl phthalate.

Advantageously, the plasticizer or plasticizers can be present in the composition in a content such that the weight ratio of the hybrid hydrophobic film-forming acrylic polymer or polymers to the plasticizer or plasticizers varies from 0.5 to 100, preferably from 1 to 50 and preferably from 1 to 10.

Thickener

The composition of use in the device or the method of the invention can comprise a thickener. This thickener can be chosen from inorganic or organic and polymeric or non-polymeric thickeners, and mixtures thereof.

The term "thickener" is understood to mean a compound which modifies the rheology of the medium into which it is incorporated.

According to a specific embodiment of the invention, the composition comprises at least one inorganic thickener.

Preferably, the thickener or thickeners is/are chosen from fumed silica, clays or mixtures thereof.

The fumed silicas can be obtained by high-temperature pyrolysis of a volatile silicon compound in an oxyhydrogen flame, producing a finely divided silica. This process makes it possible in particular to obtain hydrophilic silicas which have a large number of silanol groups at their surface. Such hydrophilic silicas are sold for example under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of said silica via a chemical reaction which brings about a reduction in the number of silanol groups. It is possible in particular to replace silanol groups with hydrophobic groups: a hydrophobic silica is then obtained.

The hydrophobic groups can be:
trimethylsiloxyl groups, which are obtained in particular by treating fumed silica in the presence of hexamethyldisilazane. Silicas thus treated are known as "Silica silylate" according to the CTFA (6$^{th}$ edition, 1995). They are sold for example under the references Aerosil R812® by Degussa and Cab-O-Sil TS-530® by Cabot.
dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6$^{th}$ edition, 1995). They are sold for example under the references Aerosil R972® and Aerosil R974® by Degussa, and Cab-O-Sil TS-610® and Cab-O-Sil TS-720® by Cabot.

The fumed silica preferably has a particle size that may be nanometric to micrometric, for example ranging from about 5 to 200 nm.

Clays are well known products which are described, for example, in the publication "Minéralogie des argiles" [Mineralogy of Clays], S. Caillère, S. Hénin and M. Rautureau, 2nd Edition, 1982, Masson.

Clays are silicates containing a cation which can be chosen from calcium, magnesium, aluminium, sodium, potassium or lithium cations, and mixtures thereof.

Mention may be made, as examples of such products, of clays of the family of the smectites, such as montmorillonites, hectorites, bentonites, beidellites or saponites, and also of the family of the vermiculites, stevensite or chlorites.

These clays can be of natural or synthetic origin. Use is preferably made of clays which are cosmetically compatible and acceptable with keratin substances.

Mention may be made, as clay which can be used according to the invention, of synthetic hectorites (also known as laponites), such as the products sold by Laporte under the name Laponite XLG, Laponite RD and Laponite RDS (these products are sodium magnesium silicates and in particular lithium magnesium sodium silicates); bentonites, such as the product sold under the name Bentone HC by Rheox; magnesium aluminium silicates, in particular hydrated, such as the product sold by R.T. Vanderbilt Company under the name Veegum Ultra, or calcium silicates and in particular that in synthetic form sold by the company CELITE ET WALSH ASS under the name Micro-Cel C.

The organophilic clay can be chosen from montmorillonite, bentonite, hectorite, attapulgite or sepiolite, and mixtures thereof. The clay is preferably a bentonite or a hectorite.

These clays can be modified with a chemical compound chosen from quaternary amines, tertiary amines, amine acetates, imidazolines, amine soaps, fatty sulfates, alkylarylsulfonates, amine oxides and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The thickener can also be chosen from organic compounds.

Mention may be made, for example, of the following polymeric or non-polymeric products: $C_{10}$-$C_{30}$ fatty amides, such as lauric acid diethanolamide, the polyglyceryl (meth)acrylate polymers sold under the names Hispagel or Lubragel by the companies Hispano Quimica or Guardian, polyvinylpyrrolidone, polyvinyl alcohol, crosslinked acrylamide polymers and copolymers, such as those sold under the names PAS 5161 or Bozepol C by Hoechst or Sepigel 305 by SEPPIC, or alternatively the crosslinked methacryloyloxyethyltrimethylammonium chloride homopolymers sold under the name Salcare SC95 by Allied Colloid, associative polymers and in particular associative polyurethanes.

Such thickeners are described in particular in Application EP-A-1 400 234.

Mention may also be made of the following thickeners, in particular if the compositions comprise oily compounds:

organophilic clays;

hydrophobic fumed silicas.

More specifically, organophilic clays are clays modified by chemical compounds which make the clay capable of swelling.

Preferably, the composition comprises at least one inorganic thickener which is preferably chosen from clays and more advantageously still from smectites, preferably bentonites.

According to a preferred embodiment, the composition of use in the invention comprises at least one thickener. This or these thickener(s) can then be present in a total content ranging from 0.1% to 10% by weight, relative to the weight of the composition.

The composition according to the invention comprises water, which can preferably be present in a content ranging from 20% to 98% by weight, relative to the weight of the composition.

According to a specific embodiment, the composition of the invention comprises an odorous compound or a mixture of odorous compounds, such as a fragrance. Mention may be made, as odorous compounds and fragrances, of those described in the article "Perfumes" by William L. Schreiber, pp 171-201, volume 18, of the fourth edition of The Encyclopedia of Chemical Technology, Kirk-Othmer, 1996.

The compositions can also comprise at least one agent commonly used in cosmetics, for example chosen from reducing agents, fatty substances, organic solvents or oils, softening agents, anti-foaming agents, moisturizing agents, UV screening agents, peptizing agents, solubilizing agents, anionic, cationic, non-ionic or amphoteric surfactants, proteins, vitamins, propellants, oxyethylenated or non-oxyethylenated waxes, paraffins or $C_{10}$-$C_{30}$ fatty acids, such as stearic acid or lauric acid.

The above additives are generally present in an amount for each of them of between 0.01% and 20% by weight, relative to the weight of the composition.

Of course, a person skilled in the art will take care to choose this or these optional additive(s) so that the advantageous properties intrinsically attached to the formation of the coating in accordance with the invention are not, or not substantially, detrimentally affected.

The composition according to the invention can be provided in particular in the form of a suspension, a dispersion, a gel, an emulsion, in particular an oil-in-water (O/W), water-in-oil (W/O) or multiple (W/O/W or polyol/O/W or O/W/O) emulsion, a cream, a foam, a stick, a dispersion of vesicles, in particular of ionic or non-ionic lipids, a two-phase or multiphase lotion, a spray or a paste. The composition can also be provided in the form of a lacquer.

A person skilled in the art can choose the appropriate formulation form, and also its method of preparation, on the basis of his general knowledge, taking into account first the nature of the constituents used, in particular their solubility in the support, and secondly the application envisaged for the composition.

The composition described above can be employed on dry or wet keratin fibres and also on any type of fibre, light or dark, natural or dyed, or permanent-waved, bleached or straightened. It can be applied according to any suitable means, for example using a brush, the fingers or with an applicator bottle.

According to a specific embodiment of the method of the invention, the fibres are washed before application of the composition described above.

After the application of the composition, the fibres can be left to dry or dried, for example at a temperature greater than or equal to 30° C. The drying, if it is employed, can be carried out immediately after the application or after a leave-in time which can range from 1 minute to 30 minutes.

Preferably, if the fibres are dried, they are dried with, in addition to a supply of heat, a stream of air. This stream of air during the drying makes it possible to improve the individualization of the coating.

During the drying, a mechanical action can be exerted on the locks, such as combing, brushing or running the fingers through the hair. This operation can likewise be carried out once the fibres have dried, naturally or otherwise.

The drying stage of the method of the invention can be carried out with a hood dryer, a hair dryer, hair straighteners or a Climazone.

When the drying stage is carried out with a hood dryer or a hair dryer, the drying temperature is between 40° C. and 110° C. and preferably between 50° C. and 90° C.

The application of the composition can be followed by a stage of shaping the fibres by means of the fingers or using a device, such as a comb, a brush, hair straighteners or a curling iron. After such a treatment of the fibres, the shaping is persistent with respect to shampooing operations.

When the drying stage is carried out with hair straighteners or a curling iron, the drying temperature is between 110° C. and 220° C. and preferably between 140° C. and 200° C.

The invention will be illustrated more fully with the aid of the non-limiting examples that follow. Unless otherwise mentioned, the amounts indicated are expressed in grams.

EXAMPLES

Composition Examples

| Composition A | |
|---|---|
| Styrene/acrylates copolymer in aqueous dispersion, sold by BASF under the name Joncryl 77 | 21.2 g, i.e. 10% as AM |
| Divinyldimethicone/dimethicone copolymer in aqueous | 8.3 g, |

| Composition A | |
|---|---|
| emulsion, sold by Dow Corning under the reference HMW 2220 Non-Ionic Emulsion | i.e. 5% as AM |
| "Trésor" fragrance from Lancome | 0.5 g |
| Water | q.s. 100 g |

The formula of composition A is deposited on a 1 g lock of hair. After a few seconds at ambient temperature, the lock of hair is dry and scented. The hair is individualized with the fingers or using a brush and/or a comb. The feel of the hair is soft and natural, and thicker to the touch (provision of mass). The mass provided to the head of hair remains present after at least a first shampooing operation. The hair remains scented at least up to the first shampooing operation.

| Composition B | |
|---|---|
| Styrene/acrylates copolymer in aqueous dispersion, sold by BASF under the name Joncryl 77 | 21.2 g, i.e. 10% as AM |
| Divinyldimethicone/dimethicone copolymer in aqueous emulsion, sold by Dow Corning under the reference HMW 2220 Non-Ionic Emulsion | 8.3 g, i.e. 5% as AM |
| Clay (Magnesium Aluminium Silicate), sold by R. T. Vanderbilt under the name Veegum granules | 2 g |
| "Trésor" fragrance from Lancome | 0.5 g |
| Water | q.s. 100 g |

The formula of composition B is deposited on a lock of fine hair. After a few seconds, the hair is dry with a provision of mass. The hair is individualized with the fingers or using a brush and/or a comb. The feel of the hair is soft and natural, and thicker to the touch. The mass provided to the head of hair remains present after at least a first shampooing operation. The hair remains scented at least up to the first shampooing operation.

The clay makes it possible to retain the fragrance for longer.

| Composition C | |
|---|---|
| Styrene/acrylates copolymer in aqueous dispersion, sold by BASF under the name Joncryl 77 | 20 g, i.e. 9.45% as AM |
| Divinyldimethicone/dimethicone copolymer in aqueous emulsion, sold by Dow Corning under the reference HMW 2220 Non-Ionic Emulsion | 7.2 g, i.e. 4.3% as AM |
| Clay (Magnesium Aluminium Silicate), sold by R.T. Vanderbilt under the name Veegum granules | 2 g |
| "Trésor" fragrance from Lancome | 0.5 g |
| Water | q.s. 100 g |

The formula of composition C is deposited on a 1 g lock of hair. After a few seconds, the lock of hair is dry and scented. The hair is individualized with the fingers or using a brush and/or a comb. The feel of the hair is soft and natural, and thicker to the touch. The mass provided to the head of hair remains present after at least a first shampooing operation. The hair remains scented at least up to the first shampooing operation.

Comparative Example

The following composition were prepared: composition D according to the invention contains a hybrid film-forming hydrophobic acrylic polymer, composition E contains a PDMS grafted alkyl methacrylate copolymer which is not hybrid.

| | D (invention) | E |
|---|---|---|
| Divinyldimethicone/dimethicone copolymer in aqueous emulsion, sold by Dow Corning under the reference HMW 2220 Non-Ionic Emulsion | 6% as AM | 6% as AM |
| Styrene/acrylates copolymer in aqueous dispersion, sold by BASF under the name Joncryl 77 | 11.75 as AM | — |
| Poly dimethylsiloxane grafted alkyl methacrylate copolymer (KP-561 P - Shin Etsu) | — | 11.75 as AM |
| Fragrance | 3.5 | 3.5 |
| Isododecane | 25 | 25 |
| Water | Qs 100 | Qs 100 |

Each composition is deposited on a lock of permanent-waved grey hair containing 90% white hairs, with 0.5 g of composition for 1 g of hair, the composition being applied uniformly all along the lock. After a few seconds, the lock of hair is dried with a hair drier and a brush, then the hair is combed.

Individualization:

after being combed, the hair treated with composition D is perfectly individualized, while the hair treated with composition E is sticked together and forms clumps.

Persistence of the Coating

An important deposit is observed on the fingers after running them through the hair lock treated with composition E. There is no deposit on the fingers with the hair treated with composition D.

After the above mentioned evaluations, the locks of hair treated with compositions D and E are washed one time with a standard shampoo.

Before the shampooing operation, the fragrance is stronger on the hair treated with composition D. After the shampooing operation, the hair treated with composition D remains scented, while the hair treated with composition E does not.

The persistence of the coating (toward shampoing operations and rubbing) is better with composition D than with comparative composition E.

The invention claimed is:

1. A non-coloring composition for treating keratin fibers comprising:
   (1) at least one aqueous dispersion of particles of at least one hybrid acrylic film-forming polymer synthesized from:
      at least one compound (i) chosen from monomers having at least one (meth)acrylic acid group and/or esters of these acid monomers and/or amides of these acid monomers, and
      at least one compound (ii) other than the compounds (i), which does not comprise (meth)acrylic acid group and/or esters of these acid monomers and/or amides of these acid monomers, and
   (2) at least one linear block silicone copolymer synthesized from:
      (a) at least one polysiloxane having at least one reactive group; and
      (b) at least one organosilicone compound,
   wherein the at least one aqueous dispersion of particles of at least one hybrid hydrophobic film-forming acrylic polymer is present in an amount, expressed as active materials, ranging from about 0.1% to about 30% by weight, relative to the total weight of the composition, wherein the at least one linear block silicone copolymer is present in an amount, expressed as active materials of polymers, ranging from about 0.1% to about 30% by weight, relative to the total weight of the non-coloring composition wherein the at least one hybrid hydrophobic film-forming acrylic polymer and the at least one linear block silicon copolymer are present in a weight ratio, as active materials, ranging from about 0.2 to about 10.

2. The non-coloring composition according to claim 1, wherein the at least one linear block silicone copolymer is in the form of particles in dispersion in an aqueous medium.

3. The non-coloring composition according to claim 1, wherein the at least one linear block silicone copolymer is obtained by a chain extension reaction, in the presence of at least one catalyst, from at least:
(a) a polysiloxane (i) having at least one reactive group per molecule; and
(b) an organosilicone compound (ii) which reacts with the polysiloxane (i) by a chain extension reaction.

4. The non-coloring composition according to claim 3, wherein the polysiloxane (i) is chosen from the compounds of formula (I):

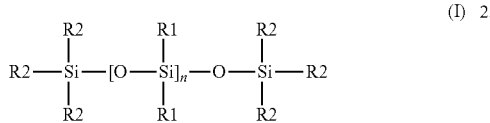
(I)

wherein $R_1$ and $R_2$ are independently chosen from hydrocarbon groups comprising from 1 to 20 carbon atoms, aryl groups and reactive groups, and n is an integer greater than 1, provided that there are on average between one and two reactive groups per polymer.

5. The non-coloring composition according to claim 4, wherein the reactive groups are chosen from hydrogen; aliphatically unsaturated groups; hydroxyl; alkoxy groups; alkoxy-alkoxy groups; acetoxy; amino groups; and mixtures thereof.

6. The non-coloring composition according to claim 4, wherein $R_1$ is a methyl group and $R_2$ at the chain end is a vinyl group.

7. The non-coloring composition according to claim 3, wherein the organosilicone compound (ii) is chosen from polysiloxanes of formula (I) and chain-extending agents.

8. The non-coloring composition of claim 7, wherein the chain-extending agents are chosen from silanes, siloxanes and silazanes.

9. The non-coloring composition according to claim 3, wherein the organosilicone compound (ii) is chosen from liquid organohydropolysiloxanes of formula (II):

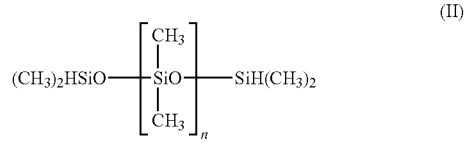
(II)

wherein n is an integer greater than 1.

10. The non-coloring composition according to claim 9, wherein n is an integer greater than 10.

11. The non-coloring composition according to claim 2, wherein the aqueous dispersion of linear block silicone copolymer is an aqueous dispersion of divinyldimethicone/dimethicone copolymer.

12. The non-coloring composition according to claim 1, wherein the at least one hybrid acrylic film-forming polymer is synthesized from at least one monomer having at least one (meth)acrylic acid group and/or esters of these acid monomers and/or amides of these acid monomers, and from at least one styrene compound.

13. The non-coloring composition according to claim 1, wherein the at least one hybrid acrylic film-forming polymer is chosen from styrene/acrylate copolymers resulting from the polymerization of at least one styrene monomer and of at least one $C_1$-$C_{10}$ alkyl acrylate monomer.

14. The non-coloring composition according to claim 1, further comprising at least one odorous compound.

15. The non-coloring composition according to claim 1, further comprising at least one inorganic thickener chosen from clays.

* * * * *